United States Patent [19]
Johnston et al.

[11] 4,450,063
[45] May 22, 1984

[54] PROBE FOR ALUMINA CONCENTRATION METER

[75] Inventors: Thomas J. Johnston, Rogersville; Nolan E. Richards, Florence; Alton T. Tabereaux, Sheffield, all of Ala.

[73] Assignee: Reynolds Metals Company, Richmond, Va.

[21] Appl. No.: 536,708

[22] Filed: Sep. 28, 1983

[51] Int. Cl.³ .................................................. G01N 27/26
[52] U.S. Cl. ................................... 204/400; 204/421; 324/433; 324/449
[58] Field of Search ................ 204/400, 421; 324/433, 324/449

[56] References Cited
U.S. PATENT DOCUMENTS

| | | | |
|---|---|---|---|
| 3,324,013 | 6/1967 | Dewing | 204/400 |
| 3,471,390 | 10/1969 | Kibby et al. | 204/195 |
| 3,476,671 | 11/1969 | Petty | 204/400 |
| 3,979,665 | 9/1976 | Ebling et al. | 324/30 R |
| 4,098,651 | 7/1978 | Alder | 204/400 |
| 4,179,349 | 12/1979 | Park | 204/400 |

*Primary Examiner*—Arthur P. Demers
*Attorney, Agent, or Firm*—Alan T. McDonald

[57] ABSTRACT

An improved probe for an alumina concentration meter is disclosed. The active anode and cathode surfaces of the probe lie on a common surface. A bath temperature measuring device is included within the probe.

10 Claims, 1 Drawing Figure

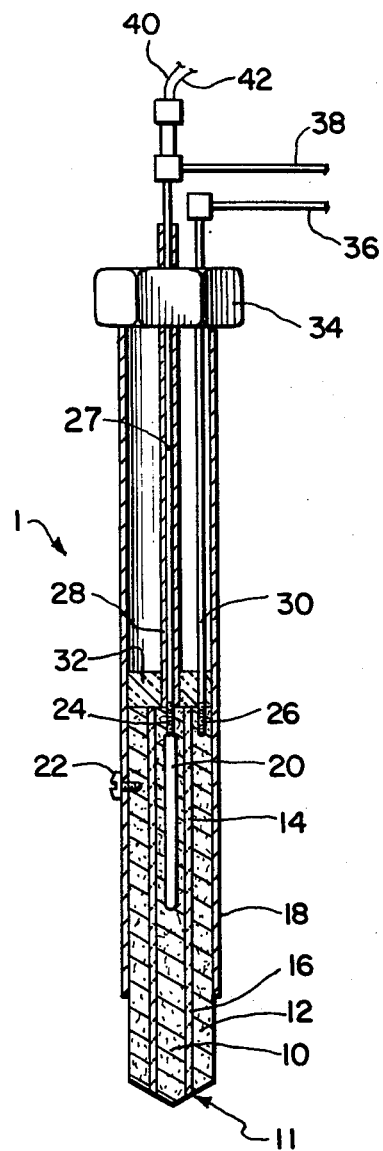

PROBE FOR ALUMINA CONCENTRATION METER

BACKGROUND OF THE INVENTION

Aluminum reduction cells or pots traditionally are controlled manually. One of the more important actions required of the operator is to initiate the feeding of alumina to the cell, with considerable judgment and background knowledge being a prerequisite on the part of the operator. Operating efficiency of the cells depend upon the percent alumina in the electrolyte, which normally ranges between approximately 1% and approximately 8%.

Industrial cells change their mode of operation when the alumina content falls to approximately 1½%, at which time an "anode effect" occurs. This anode effect requires voltage as much as 10 times normal operating voltage to force the pot having the anode effect to pass normal amperage of the potline. In a series of electrolytic cells in which there is a limitation on line voltage, an anode effect on one pot means that the voltage on the remaining pots is decreased and therefore the line current decreases slightly, for example, 2%. If several reduction cells in the line are having anode effects simultaneously, the line amperage can fall as much as 10% below normal operating levels. This reduced amperage means that the remaining cells are not producing as much aluminum as they would if the amperage were at a level which is possible when there are no anode effects in the line.

Since anode effects mean lost production and higher cost in the reduction plant, it is customary to feed alumina to the cells on a schedule such that anode effects do not occur more often than about one per day per pot. In some cell types, it is possible to suppress the anode effect even longer by scheduled feeding of alumina. The closer the operator comes to complete suppression of the anode effect, however, the closer he comes to overfeeding, which results in excessive undissolved alumina in the electrolyte. Eventually, if overfeeding is sustained, the pot becomes "sick", a condition also causing a loss of production and additionally resulting in excessive heating in the cell.

One method of determining alumina concentration is to take samples of the bath and to run chemical analysis. Disadvantages of this method are that it requires considerable cost and time during which the pot, if close to the lower limit of alumina concentration, may produce an anode effect.

It has long been desired by operators engaged in alumina reduction involving the electrolytic process to have an instrument system which would permit the direct and quick determination of the percent alumina dissolved in the cryolite electrolyte. In U.S. Pat. No. 3,471,390, the disclosure of which is hereby incorporated herein by reference, such an alumina concentration metering system is disclosed. The system includes a power supply connected to an immersible probe having anode and cathode members, means for applying voltage of increasing magnitude to the probe and means for indicating the alumina concentration of the cell corresponding to the occurrence of an abrupt increase in the resistance between the anode and cathode members of the probe, an anode effect.

While this alumina concentration metering system is effective, problems have been noticed with regard to the probe member employed therein. First, there is a relatively large distance between the active anode and cathode surfaces, which distance is increased by the fact that the anode and cathode surfaces do not lie in a common plane, requiring electrical current to flow "around a corner" from the anode to the cathode. Further, assembly problems resulted from the need to employ either a carbonaceous or a refractory cement to construct the probe in such a manner that the various components thereof, when fitted to one another, would be "bath tight" to the highly penetrating molten cryolite-alumina electrolyte bath.

It has also been found desirable to be able to determine the temperature of the bath in conjunction with the measurement of its alumina content.

THE PRESENT INVENTION

By means of the present invention, the shortcomings of the prior art alumina probes have been overcome. The improved alumina probe of the present invention comprises an anode and cathode which are separated by an insulator, with the active anode and cathode surfaces lying on a common surface. Further, the components forming the anode, cathode and insulator are assembled by force fitting, providing a "bath tight" probe without the need for carbonaceous or refractory cements, thus providing a more reliable probe. Additionally, a temperature sensor is mounted within the anode of the probe, thus enabling concurrent measurement of both bath alumina concentration and bath temperature.

BRIEF DESCRIPTION OF THE DRAWING

The improved alumina concentration probe of the present invention will be more fully described with reference to the drawing in which:

The FIGURE is a cross-sectional view of the alumina concentration probe of the present invention.

DETAILED DESCRIPTION OF THE PREFERRED EMBODIMENT

Turning now to the FIGURE, an improved alumina concentration probe 1 is illustrated. This probe 1 is operated by means of positioning the probe 1 within the electrolyte bath of an electrolytic cell and applying increasing voltages between the anode and cathode of the probe 1 until an abrupt increase in resistance between the anode and cathode of the probe 1 is realized, thus producing an "anode effect". The metering operation is more fully described and incorporated by reference U.S. Pat. No. 3,471,390, thus the details of the metering operation, which are not important to the discussion of the present invention, will not be repeated here.

The probe 1 includes a carbonaceous anode 10, which is surrounded by a refractory insulator 16, a carbonaceous cathode 12 and an outer tube 18. The anode 10 is carbonaceous, typically being formed of graphite. Insulator 16, which electrically isolates anode 10 from cathode 12, is formed from a refractory which can withstand the corrosive nature of the cryolite-alumina bath to which the probe 1 is subjected. Boron nitride is the preferred material for this insulator 16. Since, however, the entire probe 1 is not subjected to the electrolyte, an upper portion 14 of the insulator 16 may be formed of other refractory materials, such as alumina. In that case, insulator 16 would be formed of two parts. Cathode 12 is formed from the same carbonaceous materials as anode 12, preferably graphite.

In order to maintain a "bath tight" probe, insulator 16 is force fit into cathode 12 and anode 10 is force fit into insulator 16. This cannot be accomplished by hand pressure, but may be accomplished, for example, with a hydraulic press and alignment jig. Although the materials forming probe 1 are brittle, the lubricating qualities of both the boron nitride and the graphite facilitate the assembly of these components.

To accomplish this force fit, close tolerances should be maintained. Thus, the outside diameter of insulator 16 should be not more than plus or minus 0.002 inches (0.005 centimeters) than the inner diameter of cathode 12 and the diameter of the anode 10 should not be more than plus or minus 0.002 inches (0.005 centimeters) than the inner diameter of insulator 16.

Once components 10, 12 and 16 are assembled, a generally conical surface 11 is formed at the tip of probe 1. This surface 11 provides a single active working surface for both the anode 10 and the cathode 12, permitting electrical flow at close distances between these two elements, greatly increasing the reliability of the probe 1. As the probe 1 is used, the surface 11 will wear, as does the anode and cathode in a typical production reduction cell, and tip 11 may be reground several times before the need arises to replace the anode 10, insulator 16 and cathode 12.

Cathode 10 is electrically connected to the metering system (not shown) through rod 30, which is threaded at its end 26 and connected to electrical line 36 at its other end. Rod 30 may be formed of a conductive metal, such as stainless steel, Inconel or nickel.

Similarly, a rod 27, which may be formed from the same materials as rod 30, is threaded at its end 24 to anode 10 at one end thereof and connected to electrical line 38 at the other end thereof. Rod 27 lies within a tube 28, which tube 28 is formed from a non-conductive material, such as alumina, as do electrical lines 40 and 42. These electrical lines 40 and 42 are connections to a thermocouple 20 which is positioned within anode 10 and which is employed to measure the temperature of the probe 1 and thus the bath in which the probe 1 is placed.

The assembly previously described is then positioned within a housing comprising a tube 18, which tube 18 is formed from a material which must be capable of withstanding the electrolytic bath. Typical materials from which this tube 18 may be formed include stainless steel, wrought steel, Inconel and Monel. The anode-cathode assembly is held in place by means of a screw 22 which passes through tube 18 and into cathode 12. It is important that screw 22 does not pass through insulator 16, as a short circuit would then result.

Finally, an insulating material, such as finally divided metallurgical alumina, is poured over the anode-cathode assembly as layer 32, to inhibit oxidation of the anode 10 and the cathode 12 and provide thermal insulation to reduce heat losses from the top of the probe 1, so that the electrolytic bath will not freeze on surface 11. An end cap 34 is placed in position to complete the assembly. It should be noted that insulating material 32 may extend up to cap 34, if desired.

In forming the surface 11 where actual measurement occurs, it is important that the anode area of said surface 11 be at least 0.2 $cm^2$ in order that adequate reproducibility of results occur and that the surface 11 have inclined contours, such as the conical surface illustrated, and not be a horizontal, flat surface. If desired, surface 11 could be semi-spherical, however, it is much harder to form and reshape such a surface.

From the foregoing, it is clear that the present invention provides an alumina probe which overcomes the difficulties of those employed in the past.

While the invention has been described with reference to certain specific embodiments thereof, it is not intended to be so limited thereby, except as set forth in the accompanying claims.

We claim:

1. In a probe for measuring alumina concentration in a bath comprising an anode, electrical insulation surrounding said anode and a cathode surrounding said electrical insulation, the improvement wherein the working surfaces of said anode, insulation and cathode lie on a common, inclined surface.

2. The probe of claim 1 wherein said surface is conical.

3. The probe of claim 1 wherein said surface is semi-spherical.

4. The probe of claim 1 wherein the anode portion of said surface has an area of at least 0.2 $cm^2$.

5. The probe of claim 1 wherein said anode is formed from graphite.

6. The probe of claim 1 wherein said cathode is formed from graphite.

7. The probe of claim 1 wherein said insulation is formed from boron nitride.

8. The probe of claim 7 wherein a portion of said insulation which is not in contact with said bath is formed from alumina.

9. The probe of claim 1 wherein said insulation is force fit into said cathode and said anode is force fit into said insulation.

10. The probe of claim 1 further comprising a temperature sensor within said anode.

* * * * *